United States Patent [19]

Razzano et al.

[11] Patent Number: 5,670,596

[45] Date of Patent: Sep. 23, 1997

US005670596A

[54] PRODUCTION OF LOW MOLECULAR WEIGHT LINEAR HYDROGEN SILOXANES

[75] Inventors: John S. Razzano, Cohoes, N.Y.; Patricia P. Anderson, Williamstown, Mass.; Robert J. Perry, Niskayuna, N.Y.

[73] Assignee: General Electric Company, Pittsfield, Mass.

[21] Appl. No.: 623,340

[22] Filed: Mar. 27, 1996

Related U.S. Application Data

[63] Continuation-in-part of Ser. No. 294,808, Aug. 25, 1994, Pat. No. 5,510,441.

[51] Int. Cl.$^6$ .................................................. C08G 77/08
[52] U.S. Cl. ............................. 528/16; 528/14; 528/18; 528/21; 528/23; 528/31
[58] Field of Search ............................. 528/23, 21, 14, 528/16, 18, 31

[56] References Cited

U.S. PATENT DOCUMENTS

| | | |
|---|---|---|
| 2,830,967 | 4/1958 | Nitzsche et al. . |
| 3,186,967 | 6/1965 | Nitzsche et al. . |
| 3,839,388 | 10/1974 | Nitzsche et al. . |
| 3,853,934 | 12/1974 | Siciliano et al. . |
| 4,725,643 | 2/1988 | Burkhardt . |
| 4,831,174 | 5/1989 | Elms . |
| 4,888,405 | 12/1989 | Gamon et al. . |
| 4,975,510 | 12/1990 | Wegehaupt et al. . |
| 5,008,229 | 4/1991 | Schuster et al. . |
| 5,210,131 | 5/1993 | Gilson et al. ................ 528/21 |
| 5,403,909 | 4/1995 | Rubinsztajn . |
| 5,420,221 | 5/1995 | Razzano et al. ............. 528/21 |
| 5,527,873 | 6/1996 | Kobayashi et al. ........... 528/23 |

FOREIGN PATENT DOCUMENTS 2 252 969  8/1992  United Kingdom .

*Primary Examiner*—Melvyn I. Marquis
*Attorney, Agent, or Firm*—Kenneth S. Wheelock

[57] ABSTRACT

A batch or continuous process for the production of low molecular weight hydrogen siloxanes catalyzed by soluble phosphonitrilic halides or solid acid catalysts such as acid washed clays, zeolites and ion exchange resins.

20 Claims, No Drawings

PRODUCTION OF LOW MOLECULAR WEIGHT LINEAR HYDROGEN SILOXANES

CROSS-REFERENCE TO RELATED APPLICATIONS

This is a continuation-in-part of application Ser. No. 08/294,808 filed on Aug. 25, 1994, U.S. Pat. No. 5,510,441.

FIELD OF THE INVENTION

The present invention relates to a process and catalysts for use in the production of low molecular weight linear hydrogen siloxane compounds. More particularly, the process of the present invention relates to the use of linear phosphonitrilic chloride catalysts and acid treated clays and other solid acid catalysts to produce low molecular weight linear hydrogen siloxanes.

BACKGROUND OF THE INVENTION

The preparation of low molecular weight siloxanes has been practiced for several years. A wide range of catalysts have been used to prepare these materials with a reasonable reaction time and temperature. Catalysts that may be used include, among others, sulfuric acid, trifluorosulfonic acid, some Lewis acids, sodium or potassium hydroxide, tetrabutylphosphonium silanolate and some amines. A number of U.S. Patents disclose the use of phosphonitrilic compounds for the polycondensation and redistribution of low viscosity siloxane oligomers or polymers. In particular, U.S. Pat. Nos. 2,830,967; 3,186,967; 3,839,388; and 4,725,643. U.S. Pat. No. 4,975,510 discloses linear phosphonitrilic chlorides represented by the formula:

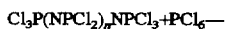

where n is an integer of from 1 to 6 are effective as catalysts for the polycondensation and equilibration of the low viscosity siloxane polymers. These catalysts have been shown to be especially effective for the production of siloxane fluids having a low content of terminal silanol groups. More recently U.S. Pat. Nos. 4,888,405 and 5,008,229 have disclosed new catalytic compositions containing phosphonitrilic chlorides and/or reaction products of these phosphonitrilic chlorides with organopolysiloxanes and/or organosilanes. A recent British Patent, 2,252,969 describes catalyst compounds having the general formula:

where E is an element having an electronegativity value of from 1.2 to 2 such as Al, Sb, P, Sn, Zn and Fe. U.S. Pat. No. 5,403,909 discloses phosphonitrilic compounds of the formula:

where b is an integer ranging from 0 to 8, a is 0 or 1, c is 0 or 1, X is a halogen selected from the group consisting of fluorine, chlorine, bromine, and iodine, Y is selected from the group consisting of OH, OR' and R'CO$_2$ where R' is alkyl or aryl; or

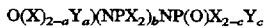

where b is an integer ranging from 0 to 8, a is 0 or 1, c is 0 or 1, X is a halogen selected from the group consisting of fluorine, chlorine, bromine, and iodine, Y is selected from the group consisting of OH, OR' and R'CO$_2$ where R' is alkyl or aryl as catalysts for the polycondensation and redistribution of siloxane polymers.

In spite of the foregoing developments, there is a continuing search for active and selective catalysts some of which may preferably be soluble in siloxanes and active for the polymerization of organosiloxanes. It is known that the application of standard linear phosphonitrilic chlorides (LPNC's) as catalysts for polycondensation of low molecular siloxanediols can produce a high molecular gum which does not contain cyclic oligomeric siloxanes and that the gum can be prepared in a short cycle time. It is also known that a mixture of high molecular weight organopolysiloxanes and low molecular weight siloxanes can be redistributed into linear polymers without formation of a significant amount of cyclic species.

Suitable catalysts for this polymerization, disproportionation or equilibration include both acids and bases. The product of these processes is a mixture of the desired product contaminated by a lesser amount of the starting material(s).

The earliest catalysts used for these processes were soluble acids or bases. Because the catalytic agent was soluble, deactivation or separation of the catalyst from the reaction products presented difficulties in downstream purification. Further, very strong acid catalysts such as sulfuric acid created problems with undesirable side reactions, such as cleavage of the organic substituents from the silicone in the polyorganosiloxane.

An early solution to the problems presented by soluble catalysts, was the use of solid catalysts. This is accomplished by resorting to the practices of heterogeneous catalysis and bonding the catalyst to a support, or alternatively using a solid material having catalytic properties, e.g. ion exchange resins. As a practical matter, ion exchange resins have been unsatisfactory from the standpoint of requiring long residence times and in addition are fairly expensive by comparison to alternative catalytic materials such as sulfuric acid and the like.

Both acid treated carbon black and acid treated clays have been used in fixed bed processes. These materials suffer from the drawback that practical conversions require fairly high temperatures. Depending on the product desired and the equilibrium relationships involved this is a greater or lesser drawback. These processes utilized temperatures ranging anywhere from 85° to 200° C. and were frequently operated at reduced pressures ranging from 5 to 200 mm Hg, particularly in the case of acid treated clays which were used in powdered, as opposed to granular, forms, because of pressure drop problems across the catalyst bed. At the lower temperatures, side reactions were minimized, but low pressures, i.e. partial vacuums, have been necessary to produce low silanol equilibrates from reactants containing high levels of silanol.

In order to reduce the problems created by increasing temperature to increase the reaction rate, the use of two beds in series was implemented (Siciliano et al. U.S. Pat. No. 3,859,934). When two fixed beds are used in series, it became possible to use less active materials such as acid treated clays as the catalysts for the equilibration polymerization reaction. The reduced activity of the acid treated hydroaluminum silicate day catalyst was partially compensated for by operating both catalyst beds at temperatures ranging from 150° to 200° C. Early developers of these processes generally were not particularly concerned with the silanol content of the resulting product nor whether the product was primarily linear or contaminated with a significant amount of branched product.

3

Later developments teaching a complete reversal of some of the preferred process parameters, e.g. a granular catalyst particles as opposed to finely divided catalyst particles, resulted in process improvements: 1) reducing the temperature range of operation to 100° to 150° C. and 2) an essentially water-free product (Elms, U.S. Pat. No. 4,891, 174). Even with these improvements, the process requires two fixed beds operated in series when utilizing acid treated clays.

Consequently two differing processes may be employed to produce low molecular weight siloxane species, one utilizing a soluble catalysts and the other utilizing a solid catalyst that may or may not employ the catalyst in a fixed bed.

When the species to be equilibrated, disproportionated, oligomerized or otherwise modified in terms of degree of polymerization is some variation of a diorganosiloxane, considerations of functional reactivity are relatively minor. However, if a hydride species is to be oligomerized, not only must the possibility of competing side reactions be considered but also the additional complicating factor due to the increased reactivity of hydride containing siloxanes relative to siloxanes that contain no active hydrogen.

Thus, solutions that might be acceptable based on a consideration of the prior art must be demonstrated to work satisfactorily because of the enhanced reactivity of hydrogen siloxanes.

SUMMARY OF THE INVENTION

The process of the present invention provides for a process for the production of hydrogen containing siloxanes of the formula:

$$M'D_x{}^H D_y M'$$

where $M'=R_{3-i}{}^1 H_i SiO_{1/2}$ being independently selected from the group of one to forty carbon atom monovalent hydrocarbon radicals and the subscript i ranges from 0 to 3;

$D^H=R_2{}^3 SiO_{2/2}$ with $R^2$ being independently selected from the group consisting of hydrogen and one to forty carbon atom monovalent hydrocarbon radicals; and $D=R_2{}^3 SiO_{2/2}$ where each $R^3$ is independently selected from the group of one to forty carbon atom monovalent hydrocarbon radicals; and the subscript x ranges from 1 to 20 and the subscript y ranges from 0 to 20; comprising:

(a) mixing a hydrogen containing siloxane selected from the group consisting of:
  i) $D_z{}^H$ where $D^H$ is as previously defined and z varies from 3 to 8; and
  ii) $M'D_{xx}{}^H D_{yy} M'$ where $M'$, $D^H$, and D are as previously defined and xx is greater than 20 and yy is either 0 or greater than 20; with (b) an M' rich silicone compound comprising M' that may also contain D, T and Q groups where M' and D are as previously defined, $T=R^4 SiO_{3/2}$ with $R^4$ being independently selected from the group of one to forty carbon atom monovalent hydrocarbon radicals, and $Q=SiO_{4/2}$ where the molar ratio of silicon atoms in the M' groups to the sum of the silicone atoms in the M', D, T, and Q groups is 0.04 or greater; in the presence of a catalyst and (c) heating the mixture of said hydrogen containing siloxane and said M' rich silicone compound to a temperature ranging from 20° C. to 200° C.

When the catalyst employed in the process of the present invention is a soluble catalyst the process further provides a process for the deactivation of the catalyst.

4

DETAILED DESCRIPTION OF THE INVENTION

The process of the present invention provides for a method of producing low molecular weight hydrogen siloxanes. More particularly the process provides higher yields of linear hydrogen siloxanes than heretofore possible. The process is made possible at either high or low temperatures by two groups of catalysts: 1) acid washed clays and other solid acid catalysts such as zeolites and ion exchange resins, and 2) linear phosphonitrilic halide catalysts, preferably a phosphonitrilic chloride.

The hydrogen siloxanes prepared by the process of the present invention are defined by the general formula:

$$M'D_x{}^H D_y M'$$

where $M'=R_{3-i}{}^1 H_i SiO_{1/2}$ with $R^1$ being an independently selected one to forty carbon atom monovalent hydrocarbon radical and the subscript i ranges from 0 to 3;

$D^H=R^2 H SiO_{2/2}$ with $R^2$ being independently selected from the group consisting of hydrogen and one to forty carbon atom monovalent hydrocarbon radicals;

$D=R_2{}^3 SiO_{2/2}$ where each $R^2$ is an independently selected one to forty carbon atom monovalent hydrocarbon radical; and the subscript x ranges from 1 to about 20 and the subscript y ranges from 0 to about 20. Preferably the subscript x ranges from 1 to about 15 and y is 0. More preferably the subscript x ranges from about 1 to 10 and y is 0. Most preferably x ranges from 1 to 8 and y is 0.

When i=1 there is the presence of hydrogen atoms in M' which is usually designated $M^H$, but which may also stand for M' when $1 \leq i \leq 3$, and not simply only when i=1. Thus $M^H$ stands for hydrogen substituted M groups when i=1, 2, or 3.

Compounds fed to the process of the present invention are selected from two groups, hydrogen containing siloxanes and silicone compounds rich in M' groups.

M' rich silicone compounds are defined as those compounds containing M' (preferably M'M') and optionally D, T or Q groups, e.g. M'DTQ, M'DT, M'DQ, M'TQ, M'Q, M'T, and M'D with M', D, T and Q as previously defined, where the molar ratio of silicon in M' groups to the molar ratio of the sum of silicon present in the M', D, T, and Q groups is equal to or greater than 0.04. It is to be understood that a one-to-one ratio of these structural components M', D, T, and Q is not to be strictly construed from reciting these general compositions. When these materials are gels they may be dissolved in a suitable solvent. The ratio of M' to the sum of M'D, T, and Q groups is such that the M' rich compound is preferred to be a liquid. Preferably the ratio of M' to the sum of M' D, T, and Q groups is equal to or greater than 0.10, more preferably greater than 0.15, and most preferably greater than 0.25. Preferred M'-rich silicones are selected from the group consisting of:

i) M'M',
ii) M'DM',
iii) M'D$_2$M', and
iv) M'D$_3$M', and
v) mixtures thereof where M' and D are as previously defined and where $T=R^4 SiO_{3/2}$ and $Q=SiO_{4/2}$ with $R^4$ being independently selected from the group of one to forty carbon atom monovalent hydrocarbon radicals.

The hydrogen siloxanes utilized by the process of the present invention are selected from the group consisting of:

i) $D_z^H$ where z ranges from 3 to 8 thereby forming a cyclic hydrogen siloxane; and ii) $M'D_a^H D_b M'$, where M', $D^H$ and D are as previously defined and the subscript a is greater than 20 and the subscript b is 0 or a positive integer; preferably the subscript b is zero.

It should be noted that if the subscript b is positive in the precursor or reactant compounds fed to the process then the subscript y will not be zero in the product produced by the process.

The M' rich compound and the hydrogen siloxane, $M'D_a^H D_b M'$, are fed to the process in varying mole ratios depending on the stoichiometric coefficients x and y desired in the product, $M'D_x^H D_y M'$, the low molecular weight hydrogen siloxane. At low values of the M': $D^H$ ratio, e.g. 1:1, a fairly broad mixture of low molecular weight compounds is obtained, where x in the formula varies from 0 (the M'M' fed) to 8, with the predominant products being those species where x is 1, 2, 3, and 4. At higher levels of the M': $D^H$ ratio, the product becomes almost predominantly the x=1 species, although it is present in a significant excess of starting reactant, M'M'. Thus depending on the ratio employed the weight or number average molecular weight (or both) of the product may be controlled. Control of the average molecular weight of the product is independent of which catalyst is used.

The process of the present invention is operable using either soluble catalysts such as the phosphonitrilic halides or solid acid catalysts such as the acid washed clays, zeolites, ion exchange resins and the like. For solid catalysts the temperature of the process is conducted in a range from 20° to 200° C, preferably from 40° to 180° C., more preferably from 50° to 160° C., and most preferably from 60° to 140° C. For soluble catalysts, e.g. linear phosphonitrilic halide catalysts, the temperature of the process is conducted in a range from 20° to 140° C., preferably from 40° to 130° C., more preferably from 50° to 120° C., and most preferably from 80° to 100° C.

The acid washed clay catalysts useful in the practice of the low temperature process of the present invention are montmorillonite clays that have been treated with sulfuric acid. The residual acidity may be neutralized by about 14 mg KOH per gm of acid washed clay as determined by a phenolphthalein endpoint. The ignition loss at 105° C. is about 14 weight percent. The surface area of these acid washed clays as determined by a BET surface area measurement is 400 m²/g, with an apparent bulk density of about 50 lbs./cu. ft. The surface areas of smectite day catalysts, montmorillonite being one example, can vary from a low of about 50 to a high of about 500 m²/g. These materials are commercially supplied by Engelhard Corporation and are available in a variety of mesh sizes, the different mesh sizes having different catalog numbers. Applicants define granular to be a Tyler mesh ranging from about 5 to about 50. A particularly preferred physical form of the catalyst is the powdered form, Filtrol-20. Other solid acid catalysts such as zeolites may also be employed.

Specific solid acid catalyst useful in the practice of the process of the present invention include but are not limited to catalysts selected from the group consisting of acid washed clays, zeolites and ion exchange resins. The specific acid washed clay is an acid washed montmorillonite. Specific zeolites are ultra-stable Y faujasite, USY, and the pentasil form of silicalite. A specific ion exchange resin are Amberlyst XN-1010™ and Amberlyst 15™ (both available from Aldrich Chemical Company).

The phosphonitrilic halides particularly useful in the practice of the low or high temperature process of the present invention are defined by the formula:

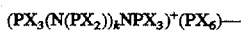

$(PX_3(N(PX_2))_k NPX_3)^+(PX_6)^-$— where X is halogen selected from the group consisting of fluorine, chlorine, bromine and iodine and k is an integer of one or greater. The preferred catalyst for the practice of the processes of the present invention is the phosphonitrilic halide, $(PX_3(N(PX_2))_k NPX_3)^+(PX_6)^-$—, where X is chlorine and k is one. The linear phosphonitrilic halide catalyst is selected from the group consisting of:

i) $(PX_3(N(PX_2))_k NPX_3)^+$ $(PX_6)^-$ where X is halogen selected from the group consisting of fluorine, chlorine, bromine and iodine and k is an integer of one or greater;

ii) $Cl_3P(NPCl_2)_n NPCl_3 + PCl_6$— where n is an integer of from 1 to 6;

iii) $Cl_3P(NPCl_2)_m NPCl_3 + ECl_p$— where E is an element having an electronegativity value of from 1.2 to 2 such as Al, Sb, P, Sn, Zn and Fe, m is an integer of from 0 to 9 and p is an integer of from 4 to 6;

iv) $O(X)_{2-g} Y_g P(NPX_2)_g NPX_{3-h} Y_h$ where g is an integer ranging from 0 to 8, f is 0 or 1, h is 0 or 1, X is a halogen selected from the group consisting of fluorine, chlorine, bromine, and iodine, Y is selected from the group consisting of OH, OR' and R'CO_2 where R' is alkyl or aryl; and v) $O(X)_{2-r} Y_r P(NPX_2)_s NP(O)X_{2-t} Y_t$ where s is an integer ranging from 0 to 8, r is 0 or 1, t is 0 or 1, X is a halogen selected from the group consisting of fluorine, chlorine, bromine, and iodine, Y is selected from the group consisting of OH, OR' and R'CO_2 where R' is alkyl or aryl.

The phosphonitrilic halide catalysts useful in the practice of the processes of the present invention may be advantageously employed at fairly low levels of concentration in the reactants ranging from about one part per billion by weight based on the combined weight of the reacting species to concentrations as high as 10,000 parts per million by weight. Preferably the range of catalyst concentration ranges from about 1 parts per million to 1,000 parts per million by weight, more preferably from about 10 part per million to about 500 parts per million by weight, and most preferably from about 25 parts per million to about 200 parts per million by weight of the reaction mixture.

An additional feature possessed by the phosphonitrilic compounds useful in the practice of the processes of the present invention is that they are susceptible of thermal deactivation. Thus it is possible to dissolve the phosphonitrilic halide catalyst in the reactants, perform the desired reactions at the process temperature of interest and then by raising the temperature of the reaction quench the activity of the catalyst by thermal deactivation. Generally this thermal quench of catalytic activity must be accomplished at temperatures in excess of 130° C., preferably at temperatures in excess of 140° C., more preferably at temperatures in excess of 150° C., and most preferably at temperatures in excess of 160° C. When the concentration of M' bearing species is high, the reflux temperature of the reaction will be lowered and thus the quench temperature will be lowered. Chemical deactivation of the soluble catalysts used in the process of the present invention may be accomplished by the addition of materials selected from the group consisting of magnesium oxide, calcium oxide, sodium carbonate, sodium bicarbonate, organic amines, and the like.

Whether solid or soluble catalysts are used to accomplish the process of the present invention, the process of the present invention may be operated in a batch or a continuous mode. Continuous processes may be accomplished in any one of several process configurations known in the art:

1) a fixed bed continuous process using a solid catalyst such as an acid washed clay, zeolite or ion exchange resin, 2) a continuous fixed bed process using a solid catalyst and a soluble catalyst, 3) a continuous stirred tank process using a solid catalyst suspended in liquid reactants, 4) a continuous stirred tank process using a soluble catalyst such as the linear phosphonitrilic halides, and 5) a continuous stirred tank process using both a soluble catalyst and a solid catalyst, and 6) a plug flow continuous process using a soluble catalyst or a slurry of a solid catalyst or mixtures thereof.

A recognized variation on the stirred tank reactor design substitutes baffles in the reaction vessel for a mechanical stirrer. These process configurations are known in the art by practitioners having ordinary skill in the art of chemical engineering. Thus continuous processes providing for product separation and reactant recycle are obvious variations of the general processes described above. Thus applicants intent the word process to include both batch and continuous modes of operation. Further, the use of low molecular weight compounds in conjunction with high temperatures may require the imposition of pressures greater than atmospheric to avoid losing a reactant by premature distillation away from the reactant mixture.

All United States patents referenced herein are herewith and hereby specifically incorporated by reference.

EXPERIMENTAL

The following examples are designed to demonstrate various embodiments of Applicants' new process and are not to be construed as limiting by virtue of being exemplary.

Example 1

To a round bottom flask equipped with a thermometer, condenser, and mechanical stirrer was charged 136.35 g of hexamethyldisiloxane, M'M' (M'D$_a{}^H$D$_b$M' where i=0 and R$^1$=CH$_3$ for M' and a and b are zero, 1.68 moles), 101.00 g of a linear hydrogen polymethylsiloxane, M'D$_x{}^H$M' (M'D$_x{}^H$D$_y$M' where i=0 and R$^1$ =CH$_3$ for M' and where x=50, y=0, and R$^2$=CH$_3$ for D$^H$; 1.68 moles), and 590 µL of a 2 weight percent solution of a linear phosphonitrilic chloride ((PX$_3$(N(PX$_2$))$_k$NPX$_3$)$^+$(PX$_6$)—, X=Cl and k=1) in a 20 cps polydimethylsiloxane oil to provide 50 parts per million by weight of the catalyst. The reaction mixture was heated to 90±5° C. for approximately one hour. Gas chromatographic analysis of the reaction mixture at 30 and 60 minute intervals showed reaction to be complete within 30 minutes. Analysis of the reaction product is presented in Table 1.

TABLE 1

Product Analysis for Synthesis of Low Molecular Weight M'DHxM'

| Component, M'DHxM' (by value of x) | Area Percent by Gas Chromatography |
|---|---|
| 0 | 18.4 |
| 1 | 23.1 |
| 2 | 18.6 |
| 3 | 13.0 |
| 4 | 8.6 |
| 5 | 5.6 |
| 6 | 3.7 |
| 7 | 23 |

The reaction mixture was subsequently heated to the reflux temperature of the mixture, 143° C., for two hours to deactivate the catalyst. As a test of catalytic activity, some of the M'M' was removed from the reaction mixture by distillation. The reaction mixture was analyzed by gas chromatography and the reaction mixture reheated to 141° C. for one hour. The reaction mixture was again analyzed by gas chromatography. The similarity of the results, presented in Table 2, confirms the loss of catalytic activity by the thermal deactivation of heating the mixture to temperature in excess of 130° C.

TABLE 2

Thermal Deactivation of Linear Phosphonitrilic Chloride Catalyst

| Component, M'DHxM' (by value of x) | Area Percent by Gas Chromatography before reflux | Area Percent by Gas Chromatography after reflux |
|---|---|---|
| 0 | 15.0 | 15.6 |
| 1 | 22.9 | 23.1 |
| 2 | 18.5 | 18.7 |
| 3 | 13.1 | 13.3 |
| 4 | 8.9 | 9.1 |
| 5 | 6.0 | 6.1 |
| 6 | 3.9 | 3.9 |
| 7 | 2.4 | 2.5 |
| 8 | 1.6 | 1.7 |
| 9 | 1.0 | 1.0 |
| 10 | 0.6 | 0.6 |

Example 2

Example 1 was repeated using 350 g of a linear hydrogen polymethylsiloxane, M'D$_x{}^H$M' (M'D$_x{}^H$D$_y$M' where i=1 and R$^1$=CH$_3$ for M' and where x=50, y=0, and R$^2$=CH$_3$ for D$^H$; 5.83 moles), 2,835 g of hexamethyldisiloxane, M'M' (M'D$_a{}^H$D$_b$M' where i=0 and R$^1$=CH$_3$ for M' and a and b are zero, 35.0 moles), and 4.78 g of a 2 weight percent solution of a linear phosphonitrilic chloride ((PX$_3$(N(PX$_2$))$_k$NPX$_3$)$^+$ (PX$_6$)—, X=Cl and k=1) in a 20 cps polydimethylsiloxane oil to provide 30 parts per million by weight of the catalyst. The reaction mixture was heated to 95°–98° C. for approximately 40 minutes. The catalyst was then deactivated by the addition of 0.40 g of magnesium oxide. The unreacted M'M' was then distilled away from the product. Gas chromatographic analysis of the reaction mixture is presented in Table 3.

TABLE 3

Product Analysis for Synthesis of Low Molecular Weight M'DHxM' after Distillation

| Component, M'DHxM' (by value of x) | Area Percent by Gas Chromatography |
|---|---|
| 0 | 1.7 |
| 1 | 73.4 |
| 2 | 17.5 |
| 3 | 3.6 |
| 4 | 0.7 |

Example 4

The procedure used in examples 1 and 2 was repeated with the following variations as summarized in Table 4.

TABLE 4

Preparative Variations to Produce Low Molecular Weight Hydrogen Siloxanes using Linear Phosphonitrilic Halide Catalyst

| Reactant or Condition | Example 4 | Example 5 | Example 6 | Example 7 | Example 8 |
|---|---|---|---|---|---|
| Weight of $((CH_3)_3Si)_2O$ | 100 | 100 | 100 | 3,000 | 100 |
| Weight of cyclic $(CH_3HSiO)_x$ grams | 6.18 | 7.39 | 7.39 | 222 | 9.24 |
| 2 wt. % LPNC sol'n, µL or g | 350 µL | 350 | 175 µL | 8.0 g | 275 µL |
| Reaction Temp., °C. | 60 | 60 | 60 | 60 | 60 |
| Reaction Time, hrs. | 3.5 | 3.5 | 8 | 5 | 3 |

| Reactant or Condition | Example 9 | Example 10 | Example 11 | Example 12 |
|---|---|---|---|---|
| Weight of $((CH_3)_3Si)_2O$ | 50 | 50 | 50 | 1,766 |
| Weight of cyclic $(CH_3HSiO)_x$ grams | 18.5 | 9.24 + 9.24 g of $M'D_x^HM'^2$ | 37.0 | 1,225 of $M'D_x^HM'^1$ |
| 2 wt. % LPNC sol'n, µL or g | 0.34 g + 0.17 g after 2 hrs. | 0.34 g + 0.22 g after 5 hrs. | 750 µL + 300 µL after 4 hrs. | 27.6 g |
| Reaction Temp., °C. | 80 | 80 | 80 | 80 |
| Reaction Time, hrs. | 2 + 4 | 5 + 3 | 4 + 3 | 8.5 |

Notes to Table 4:
1. $M'D_x^HM'$ represents a mixture of trimethylsilyl (M', where i = 1 and $R^1$ = $CH_3$) endcapped linear methylhydrogen siloxanes of the formula $M'D_x^HM'$ with a distribution of oligomers as follows: x = 1, 4.6%; x = 2, 48.4%; x = 3, 23.3%; x = 4, 11.2%, x = 5, 5.9%; x ≧ 6, 4.6%.
2. $M'D_x^HM'$ is $M'D_x^HDyM'$ where i = 0 and $R^1$ = $CH_3$ for M' and where x > 50, y = 0, and $R^2$ = $CH_3$ for $D^H$.

Examples 1–12 demonstrate the differing ratios of the low molecular weight hydrogen siloxanes that may be accomplished by varying the M' to $D^H$ ratio in the reacting mixture, when the reaction is catalyzed by linear phosphonitrilic halide catalysts. This variation is summarized in Table 5.

TABLE 5

Production of Low Molecular Weight Hydrogen Siloxanes, $M'D_x^HM'$, as a Function of $M:D^H$ Ratio Catalyzed by Linear Phosphonitrilic Halide

| $M:D^H$ Ratio Component, M'DHxM' (by value of x) | 1:1 | 2:1 | 5:1 | 10.1 |
|---|---|---|---|---|
| 0 | 18.4 | 35.9 | 63.2 | 78.2 |
| 1 | 23.1 | 30.2 | 26.1 | 17.8 |
| 2 | 18.6 | 16.6 | 7.1 | 2.8 |
| 3 | 13.0 | 7.7 | 1.7 | 0.3 |
| 4 | 8.6 | 3.4 | 0.4 | ND |
| 5 | 5.6 | 1.5 | ND | ND |
| 6 | 3.7 | 0.6 | ND | ND |
| 7 | 2.3 | 0.3 | ND | ND |

Notes to Table 5: ND = not detected

Examples 13–20

The procedure of examples 1 and 2 was followed substituting Filtrol-20, a solid catalyst, for the soluble linear phosphonitrilic halide catalyst previously used. The various quantities of reactants and reaction conditions are summarized in Table 6.

TABLE 6

Preparative Variations to Produce Low Molecular Weight Hydrogen Siloxanes using Filtrol-20 Catalyst

| Reactant or Condition | Example 13 | Example 14 | Example 15 | Example 16 | Example 17 |
|---|---|---|---|---|---|
| Weight of $((CH_3)_3Si)_2O$ | 100 | 100 | 100 | 100 | 100 |
| Weight of cyclic $(CH_3HSiO)_x$ grams | 3.72 | 6.18 | 9.24 | 12.3 | 18.48 |
| Weight of Filtrol-20, grams | 1.1 | 1.1 | 1.1 | 1.1 | 1.1 |
| Reaction Temp., °C. | 60 | 60 | 60 | 60 | 60 |
| Reaction Time, hr. | 3.5 | 3.5 | 4 | 4 | 4 |

| Reactant or Condition | Example 18 | Example 19 | Example 20 |
|---|---|---|---|
| Weight of $((CH_3)_3Si)_2O$ | 100 | 100 | 50 |
| Weight of cyclic $(CH_3HSiO)_x$ grams | 37.0 | 37.0 | 37.0 |
| Weight of Filtrol-20, grams | 1.4 | 1.1 | 0.87 |
| Reaction Temp., °C. | 60 | 120 | 80 |
| Reaction Time, hr. | 4 | 2 | 8 |

Examples 13–20 demonstrate the differing ratios of the low molecular weight hydrogen siloxanes that may be accomplished by varying the M' to $D^H$ ratio in the reacting mixture, when the reaction is catalyzed by a solid catalyst such as Filtrol-20. This variation is summarized in Table 7.

TABLE 7

Production of Low Molecular Weight Hydrogen Siloxanes, $M'D_x^HM'$, as a Function of $M:D^H$ Ratio Catalyzed by Filtrol-20 Catalyst

| $M:D^H$ Ratio Component, M'DHxM' (by value of x) | 1:1 | 2:1 | 4:1 | 6:1 | 8:1 | 12:1 | 20:1 |
|---|---|---|---|---|---|---|---|
| 0 | 16.4 | 36.8 | 55.8 | 66.3 | 70.9 | 79.3 | 86.7 |
| 1 | 20.8 | 30.9 | 29.3 | 24.9 | 20.7 | 15.0 | 10.9 |
| 2 | 17.3 | 16.9 | 9.7 | 5.9 | 3.8 | 2.0 | 0.9 |
| 3 | 12.3 | 8.3 | 2.8 | 1.2 | 0.6 | 0.2 | ND |
| 4 | 8.3 | 3.7 | 0.8 | 0.2 | 0.1 | ND | ND |
| 5 | 5.4 | 1.9 | 0.2 | ND | ND | ND | ND |
| 6 | 3.4 | 0.7 | ND | ND | ND | ND | ND |
| 7 | 2.3 | ND | ND | ND | ND | ND | ND |
| 8 | 1.4 | ND | ND | ND | ND | ND | ND |

Notes to Table 7:
1. ND = not detected.
2. For the 2:1 ratio experiment run at 120° C., example 19, the results were approximately identical within experimental error

Example 21

A 300 mL, 3-neck, round bottom flask, equipped with a thermometer, condenser, and a stir bar was charged with 37.0 g methylhydrogen cyclosiloxanes, 100.0 g hexamethyldisiloxane and 1.37 g of Amberlyst 15™. The reactants were heated together at 60° C. for 3 hours under nitrogen and the products analyzed by gas chromatography. The results are presented in Table 8.

Example 22

A 300 mL, 3-neck, round bottom flask, equipped with a thermometer, condenser, and a stir bar was charged with 37.0 g methylhydrogen cyclosiloxanes, 100.0 g hexamethyldisiloxane and 1.37 g of Amberlyst XN-1010™. The reactants were heated together at 60° C. for 3 hours under nitrogen and the products analyzed by gas chromatography. The results are presented in Table 8.

Example 23

A 300 mL, 3-neck, round bottom flask, equipped with a thermometer, condenser, and a stir bar was charged with 37.0 g methylhydrogen cyclosiloxanes, 100.0 g hexamethyldisiloxane and 1.37 g of ultra-stable Y faujasite (USY) available from United Catalysts. The reactants were heated together at 60° C. for 24 hours under nitrogen and the products analyzed by gas chromatography. The results are presented in Table 8.

Example 24

A 300 mL, 3-neck, round bottom flask, equipped with a thermometer, condenser, and a stir bar was charged with 37.0 g methylhydrogen cyclosiloxanes, 100.0 g hexamethyldisiloxane and 1.37 g of pentasil silicalite available from United Catalysts. The reactants were heated together at 60° C. for 24 hours under nitrogen and the products analyzed by gas chromatography. The results are presented in Table 8.

TABLE 8

| Example: | 21 | 22 | 23 | 24 |
|---|---|---|---|---|
| Catalyst: | Amberlyst-15 | Amberlyst XN-101 | USY | pentasil |
| Component, M'DHxM' (by value of x) | | | | |
| 0 | 38.8 | 38.2 | 50.2 | 48.1 |
| 1 | 30.0 | 31.9 | 23.8 | 25.3 |
| 2 | 15.8 | 17.0 | 8.6 | 9.9 |
| 3 | 7.6 | 7.8 | 5.6 | 6.2 |
| 4 | 3.8 | 3.5 | 5.2 | 5.4 |
| 5 | 2.0 | 1.5 | 3.5 | 3.4 |
| 6 | 0.9 | <1.0 | 1.5 | 1.6 |
| $D^H_4$ (cyclictetramer) | | | 1.3 | 1.0 |

Having described the invention that which is claimed is:

1. A process for the production of hydrogen containing siloxanes of the formula:

$$M'D_x{}^HD_yM'$$

where $M'=R_{3-i}{}^1H_iSiO_{1/2}$ with $R^1$ being independently selected from the group of one to forty carbon atom monovalent hydrocarbon radicals and the subscript i ranges from 0 to 3;

$D^H=R^2HSiO_{2/2}$ with $R^2$ being independently selected from the group consisting of hydrogen and one to forty carbon atom monovalent hydrocarbon radicals; and $D=R_2{}^3SiO_{2/2}$ where each $R^3$ is independently selected from the group of one to forty carbon atom monovalent hydrocarbon radicals; and the subscript x ranges from 1 to 20 and the subscript y ranges from 0 to 20; comprising:

(a) mixing a hydrogen containing siloxane selected from the group consisting of:
   i) $D_z{}^H$ where $D^H$ is as previously defined and z varies from 3 to 8; and
   ii) $M'D_{xx}{}^HD_{yy}M'$ where $M'$, $D^H$, and D are as previously defined and xx is greater than 20 and yy is either 0 or greater than 20;  with (b) an M' rich silicone compound comprising M' where M' is as previously defined, wherein when said M' rich compound additionally comprises D, T, or Q groups, D is as previously defined, $T=R^4SiO_{3/2}$ with $R^4$ being independently selected from the group of one to forty carbon atom monovalent hydrocarbon radicals, and $Q=SiO_{4/2}$ where the molar ratio of silicon atoms in the M' groups in said M' rich silicone compound to the sum of the silicone atoms in the M', D, T, and Q groups in said M' rich silicone compound is 0.04 or greater; in the presence of a catalyst selected from the group consisting of acid washed clays, zeolites, ion exchange resins and linear phosphonitrilic halides and (c) heating the mixture of said hydrogen containing siloxane and said M' rich silicone compound to a temperature ranging from 20° C. to 200° C.

2. The process of claim 1 wherein said catalyst is a solid catalyst selected from the group consisting of
   1) acid washed clays,
   2) zeolites, and
   3) ion exchange resins.

3. The process of claim 2 where the temperature ranges from 40° C. to 180° C.

4. The process of claim 3 where the catalyst is an acid washed clay.

5. The process of claim 3 where the catalyst is a zeolite.

6. The process of claim 3 where the catalyst is an ion exchange resin.

7. The process of claim 1 where the catalyst is a linear phosphonitrilic halide.

8. The process of claim 7 where the temperature ranges from 20° C. to 140° C.

9. The process of claim 8 where the linear phosphonitrilic halide is selected from the group consisting of:
   i) $(PX_3(N(PX_2))_kNPX_3)^+(PX_6)^-$ where X is halogen selected from the group consisting of fluorine, chlorine, bromine and iodine and k is an integer of one or greater;
   ii) $Cl_3P(NPCl_2)_nNPCl_3{}^+PCl_6{}^-$ where n is an integer of from 1 to 6;
   iii) $Cl_3P(NPCl_2)_mNPCl_3{}^+ECl_p{}^-$ where E is an element having an electronegativity value of from 1.2 to 2, m is an integer of from 0 to 9 and p is an integer of from 4 to 6;
   iv) $O(X)_{2-f}Y_fP(NPX_2)_gNPX_{3-h}Y_h$ where g is an integer ranging from 0 to 8, f is 0 or 1, h is 0 or 1, X is a halogen selected from the group consisting of fluorine, chlorine, bromine, and iodine, Y is selected from the group consisting of OH, OR' and R'CO$_2$ where R' is alkyl or aryl; and
   v) $O(X)_{2-r}Y_rP(NPX_2)_sNP(O)X_{2-t}Y_t$ where s is an integer ranging from 0 to 8, r is 0 or 1, t is 0 or 1, X is a halogen selected from the group consisting of fluorine, chlorine, bromine, and iodine, Y is selected from the group consisting of OH, OR' and R'CO$_2$ where R' is alkyl or aryl.

10. The process of claim 9 where the catalyst is $(PX_3(N(PX_2))_kNPX_3)^+(PX_6)^-$.

11. The process of claim 9 where the catalyst is $Cl_3P(NPCl_2)_nNPCl_3^+PCl_6^-$.

12. The process of claim 9 where the catalyst is $Cl_3P(NPCl_2)_mNPCl_3^+ECl_p^-$.

13. The process of claim 9 where the catalyst is $$O(X)_{2-f}Y_fP(NPX_2)_eNPX_{3-h}Y_h.$$

14. The process of claim 9 where the catalyst is $$O(X)_{2-r}Y_rP(NPX_2)_eNP(O)X_{2-r}Y_r.$$

15. The process of claim 9 further comprising deactivating said linear phosphonitrilic halide catalyst by heating to a temperature above 140° C.

16. The process of claim 15 where the amount of said linear phosphonitrilic halide catalyst ranges from 1 to 1,000 parts per million by weight of the reaction mixture.

17. The process of claim 1 where i=0 and $R^1$, $R^2$, $R^3$ and $R^4$ are each methyl.

18. The process of claim 1 where i=1 and $R^1$, $R^2$, $R^3$ and $R^4$ are each methyl.

19. The process of claim 1 where i=0, yy=0 and $R^1$, $R^2$, $R^3$ and $R^4$ are each methyl and the catalyst is an acid washed clay.

20. A process for the production of hydrogen containing siloxanes of the formula:

$$M'D_x{}^HD_yM'$$

where $M'=R_{3-i}{}^1H_iSiO_{1/2}$ with $R^1$ being independently selected from the group of one to forty carbon atom monovalent hydrocarbon radicals and the subscript i ranges from 0 to 3;

$D^H=R_2{}^3SiO_{2/2}$ with $R^2$ being independently selected from the group consisting of hydrogen and one to forty carbon atom monovalent hydrocarbon radicals; and $D=R_2{}^3SiO_{2/2}$ where each $R^3$ is independently selected from the group of one to forty carbon atom monovalent hydrocarbon radicals; and the subscript x ranges from 1 to 20 and the subscript y ranges from 0 to 20; consisting essentially of:

(a) mixing a hydrogen containing siloxane selected from the group consisting of:
 (i) $D_z{}^H$ where $D^H$ is as previously defined and z varies from 3 to 8; and
 (ii) $M'D_{xx}{}^HD_{yy}M'$ where M', $D^H$, and D are as previously defined and xx is greater than 20 and yy is either 0 or greater than 20; with (b) an M' rich silicone compound comprising M' where M' is as previously defined, wherein when said M' rich compound additionally comprises D, T, or Q groups, D is as previously defined, $T=R^4SiO_{3/2}$ with $R^4$ being independently selected from the group of one to forty carbon atom monovalent hydrocarbon radicals, and $Q=SiO_{4/2}$ where the molar ratio of silicon atoms in the M' groups in said M' rich silicone compound to the sum of the silicone atoms in the M', D, T, and Q groups in said M' rich silicone compound is 0.04 or greater; in the presence of a catalyst selected from the group consisting of acid washed clays, zeolites, ion exchange resins and linear phosphonitrilic halides and (c) heating the mixture of said hydrogen containing siloxane and said M' rich silicone compound to a temperature ranging from 20° C. to 200° C.

* * * * *